United States Patent
Austin et al.

(10) Patent No.: US 8,969,050 B2
(45) Date of Patent: Mar. 3, 2015

(54) PURIFICATION METHODS AND SYSTEMS RELATED TO RENEWABLE MATERIALS AND BIOFUELS PRODUCTION

(71) Applicants: Glen Austin, San Diego, CA (US);
Binita X. Bhattacharjee, Richmond, CA (US); Leslie W. Bolton, Hampshire (GB); Jacob Borden, San Diego, CA (US); Martin E. Carrera, Berkeley, CA (US); Amit A. Gokhale, El Cerrito, CA (US); Chris Horler, London (GB); Aidan Hurley, East Riding of Yorkshire (GB); Eric T. Mack, Newark, NJ (US)

(72) Inventors: Glen Austin, San Diego, CA (US);
Binita X. Bhattacharjee, Richmond, CA (US); Leslie W. Bolton, Hampshire (GB); Jacob Borden, San Diego, CA (US); Martin E. Carrera, Berkeley, CA (US); Amit A. Gokhale, El Cerrito, CA (US); Chris Horler, London (GB); Aidan Hurley, East Riding of Yorkshire (GB); Eric T. Mack, Newark, NJ (US)

(73) Assignee: BP Corporation North America Inc., Houston, TX (US)

( * ) Notice: Subject to any disclaimer, the term of this patent is extended or adjusted under 35 U.S.C. 154(b) by 56 days.

(21) Appl. No.: 13/682,903

(22) Filed: Nov. 21, 2012

(65) Prior Publication Data

US 2013/0130335 A1 May 23, 2013

Related U.S. Application Data

(60) Provisional application No. 61/588,896, filed on Jan. 20, 2012, provisional application No. 61/562,702, filed on Nov. 22, 2011.

(51) Int. Cl.

| | | |
|---|---|---|
| *C12P 7/16* | (2006.01) | |
| *C12P 7/04* | (2006.01) | |
| *C12P 5/00* | (2006.01) | |
| *C12P 7/64* | (2006.01) | |
| *C12M 1/00* | (2006.01) | |
| *C12P 7/06* | (2006.01) | |

(52) U.S. Cl.
CPC ... *C12P 7/16* (2013.01); *C12P 7/04* (2013.01); *C12P 5/00* (2013.01); *C12P 7/649* (2013.01); *C12M 43/02* (2013.01); *C12P 7/06* (2013.01); *Y02E 50/10* (2013.01); *Y02E 50/13* (2013.01); *Y02E 50/17* (2013.01); *Y02T 50/678* (2013.01)
USPC ........... 435/134; 435/157; 435/160; 435/161; 435/303.1

(58) Field of Classification Search
CPC ........... C12M 43/02; C12M 1/00; C12P 5/00; C12P 7/04; C12P 7/06; C12P 7/16; C12P 7/649
See application file for complete search history.

(56) References Cited

U.S. PATENT DOCUMENTS 6,872,314 B2 * 3/2005 Boyd et al. .................... 210/635
8,017,366 B1 9/2011 Schuh et al.

FOREIGN PATENT DOCUMENTS

GB 2 054 563 6/1980
WO WO 2011/094614 8/2011

OTHER PUBLICATIONS

W. Armarego et al., Purification of Laboratory Chemicals, 2009, Elsevier Inc., XP002692205.
R. Rapier, R-Squared Energy Blog. XP002692204, May 12, 2006, http://robertrapier.wordpress.com2006/05/01/bio-butanol-2/.

* cited by examiner

*Primary Examiner* — Suzanne M Noakes
*Assistant Examiner* — Gerard LaCourciere
(74) *Attorney, Agent, or Firm* — John P. Poliak; Kelly L. Cummings

(57) ABSTRACT

Methods of producing renewable materials may include consuming a fermentation feedstock with a fermentation organism to produce a renewable material in fermentation broth; water may then be separated from the feedstock or broth using one or more phase separations, or the renewable material may be concentrated from the feedstock or broth using one or more phase separations. Methods of producing biofuel components may include consuming a lignocellulosic or sugar fermentation feedstock with a fermentation organism to produce either ethanol or butanol in fermentation broth; cooling the feedstock or broth to solidify at least some water therein; and separating the solidified water from the feedstock or broth using a solid-liquid phase separation.

15 Claims, 9 Drawing Sheets

PURIFICATION METHODS AND SYSTEMS RELATED TO RENEWABLE MATERIALS AND BIOFUELS PRODUCTION

This application claims the benefit of U.S. Provisional Application No. 61/588,896 filed on Jan. 20, 2012 which claims benefit to U.S. Provisional Application No. 61/562,702 filed on Nov. 22, 2011. The entire disclosure of U.S. Provisional Application Nos. 61/588,896 and 61/562,702 are hereby incorporated by referenced into this specification.

BACKGROUND

1. Technical Field

The invention relates to purification methods and systems related to renewable materials and biofuels production. Aspects of the invention relate to the recovery of products from a fermentation process.

2. Discussion of Related Art

Renewable materials can be derived from biotic feedstocks in a process such as by fermentation. Biotic feedstocks include polysaccharide-containing plants, such as sugarcane, lignocellulosic biomass, corn, wheat, and others. Fermentation is catalyzed by micro-organisms grown in fermentation broth, where the fermentation broth includes sugars derived at least in part from the polysaccharides of the biotic feedstock. Micro-organism activity and efficiency are generally susceptible to the conditions of the fermentation broth, such as the pH and the presence of organic acids, salts, metals, and vitamins. The renewable material produced is often inhibitory to microbial activity, such as with fermentation to produce alcohols. As a fermentation progresses, inhibitory levels of the renewable material can be reached at low product concentrations. For example, typical product concentrations at which significant inhibition occurs for ethanol and butanol fermentations are 10% by weight and 2% by weight, respectively.

Purification of renewable materials from low concentrations requires considerable equipment, and also significantly affects the overall energy-integration of a fermentation process. Renewable materials can be purified by several means including by boiling point difference, such as distillation. Distillation, such as distillation of a renewable material with a lower boiling point than water, includes heating the fermentation broth to above the boiling point of the renewable material and condensing the hot vapors of concentrated renewable material.

Purification of renewable materials from low concentration fermentations can be accomplished but with significant expenditure of equipment and energy. There is a need and desire for more efficient processes and systems for purifying renewable materials. There is a further need and desire for processes and systems for converting biomass to biofuels that require minimal energy.

SUMMARY

The invention is directed to methods and systems for producing biofuels and other renewable materials, as well as biofuel component compositions made according to such methods.

According to some embodiments, a method of producing a renewable material may be achieved by consuming at least a portion of a fermentation feedstock with a fermentation organism to produce a renewable material in fermentation broth, the fermentation feedstock and/or fermentation broth comprising water. The method also includes separating at least a portion of the water from the fermentation feedstock or fermentation broth using one or more phase separations. Separating the water from the fermentation feedstock or fermentation broth may include a solid-liquid separation, a liquid-liquid separation, a vapor-liquid separation, both a solid-liquid separation and a liquid-liquid separation, or both a vapor-liquid separation and a liquid-liquid separation.

The method may also include removing enthalpy from the fermentation feedstock and/or fermentation broth, such as through an endothermic reaction. In particular, the method may include lowering a temperature of the fermentation feedstock and/or the fermentation broth below an incipient crystallization temperature, or below a binary eutectic point, or below a ternary eutectic point, or below a quaternary eutectic point.

The method may further include solidifying or crystallizing one or more components of the fermentation feedstock and/or fermentation broth. Such components may include water, alcohol, ethanol, propanol, butanol, organic acids, acetic acid, acetate, sodium acetate, calcium acetate, lactic acid, sodium lactate, calcium lactate, inorganic acids, sulfuric acid, nitric acid, aldehydes, furfural, 5-hydroxymethyl furfural, lignin, acid-soluble lignin, and/or acid-insoluble lignin. Fluidized bed heat exchangers may be used to carry out the crystallization. Additionally or alternatively, the method may include solidifying the water.

According to some embodiments, the method may include adding enthalpy to the fermentation feedstock and/or fermentation broth. For example, the method may include raising a temperature of the fermentation feedstock and/or the fermentation broth, for example raising the temperature to or above a boiling point of the renewable material and generating a vapor enriched in renewable material. As another example, the method may include lowering a pressure of the fermentation feedstock and/or the fermentation broth to or below the saturation pressure of the fermentation broth and generating a vapor enriched in renewable material. Additionally, the vapor may be condensed to form two liquid phases. A first liquid phase may be substantially at the solubility limit of water in the renewable material, while a second liquid phase may be substantially at the solubility limit of the renewable material in water. The two liquid phases may be separated, whereupon the first liquid phase may be returned to the step of generating the vapor enriched in renewable material. The method may further include generating a second vapor from the second liquid phase. Generation of the second vapor may occur at a reduced pressure. Furthermore, heat that is at least partially derived from condensing the first vapor may be used to generate the second vapor.

Renewable materials generated by fermentation include biofuels, such as alcohols. Some alcohols such as ethanol are infinitely soluble in water. Still other alcohols such as butanol have only limited solubility in water and at concentrations above the solubility limit form two phases, one phase enriched for alcohol and one phase enriched for water. Evaporation of a mixture of butanol and water above about 0.5 weight percent butanol but below the solubility limit of butanol can generate a vapor product that, upon condensation, forms a two-phase solution. In addition, the solubility of alcohols such as butanol is dependent on temperature, such as that shown in FIG. 5 for isobutanol in water.

In certain embodiments, the method may include pre-processing the fermentation feedstock and/or fermentation broth prior to phase separation.

The method may also include separating broth particulates from the fermentation feedstock and/or fermentation broth.

The step of separating at least a portion of the water from the fermentation feedstock or fermentation broth may occur in a single stage or in multiple stages, and may include such techniques as fractional freezing and/or re-slurrying. This separation step may occur substantially simultaneously with at least a portion of, or substantially after, the step of consuming at least a portion of the fermentation feedstock.

The step of consuming at least a portion of the fermentation feedstock may occur under batch fermentation, under fed-batch fermentation, under continuous fermentation, or under semi-continuous fermentation, or other appropriate fermentation method.

Similarly, the step of separating at least a portion of the water from the fermentation feedstock or fermentation broth may occur under batch operation, under fed-batch operation, under continuous operation, or under semi-continuous operation.

The phase separation of this method may include freeze-concentration and distillation, with the heat of freeze-concentration at least partially integrated with the heat of distillation. Freeze-concentration or freeze-crystallization includes cooling the fermentation broth such that water preferentially solidifies while the renewable material remains substantially in the liquid phase.

The fermentation feedstock may include carbohydrates, sugars derived at least in part from polysaccharides, sugar monomers, sugar dimers, sugar oligomers, sugars, sugars derived at least in part from plant cell walls, and/or sugars derived at least in part from storage polysaccharides.

The renewable material may, for example, include material suitable for use as biofuels, blendstocks, chemicals, intermediates, solvents, adhesives, polymers, and/or lubricants. More particularly, the renewable material may include one or more biofuel components. For example, the renewable material may include an alcohol, such as ethanol, butanol, or isobutanol, or lipids. The biofuel may include gasoline, diesel, jet fuel, and/or kerosene.

Separating at least a portion of the water from the fermentation feedstock or fermentation broth may occur at a temperature from about 0° C. to about −100° C., such as at about −20° C. Where multiple steps are used in the separation of the component, for example water, from the fermentation broth, product or feedstock, one or more of the separation steps may occur within the above temperature range. In some examples, other separation steps may occur at a temperature outside that range. For example, a stepped separation method may include cooling. Furthermore, this separation step may occur above atmospheric pressure, or substantially at atmospheric pressure, or below atmospheric pressure.

Various techniques or devices may be used to separate at least a portion of the water from the fermentation feedstock or fermentation broth, such as using rotating equipment, a centrifuge, a filtering device, gravity sedimentation or decantation, a wash column, or by solidifying the water.

The fermentation organism may include, for example, fungi, bacteria, algae, and/or yeast.

Separating at least a portion of the water from the fermentation feedstock or fermentation broth may result in a concentration of renewable material of at least 20%, or at least 3 times the concentration of the fermentation broth.

The method may also include an additional purification step. The additional purification step may result in a concentration of renewable material of at least 95%. Additionally or alternatively, the additional purification step may result in an anhydrous renewable material. The additional purification step may be carried out using molecular sieves, azeotropic distillation, or liquid-liquid extraction, for example.

According to some embodiments, a method of producing a renewable material may be achieved by consuming at least a portion of a fermentation feedstock with a fermentation organism to produce a renewable material in fermentation broth, the fermentation feedstock and fermentation broth comprising water. The method also includes concentrating at least a portion of the renewable material from the fermentation feedstock or fermentation broth using one or more phase separations. Concentrating the renewable material from the fermentation feedstock or fermentation broth may include a liquid-liquid separation, or both a solid-liquid separation and a liquid-liquid separation.

The fermentation broth may include renewable material at a concentration below a solubility limit of the renewable material in water. In certain embodiments, concentrating the renewable material from the fermentation feedstock or fermentation broth may include mixing the fermentation broth with a second solution, wherein the second solution includes water at a concentration substantially below the solubility limit of water in the renewable material. The method may further include forming two liquid phases. For example, a first liquid phase may be substantially at the solubility limit of water in the renewable material, and a second liquid phase may be substantially at the solubility limit of the renewable material in water.

According to some embodiments, a method of producing a renewable feedstock may include removing at least a portion of water by phase separation prior to fermentation.

According to some embodiments, the invention may be directed to a renewable material made according to any of the methods described herein.

According to some embodiments, a method of producing a biofuel component may be achieved by consuming at least a portion of a lignocellulosic fermentation feedstock with a fermentation organism to produce ethanol in fermentation broth, the fermentation feedstock and fermentation broth comprising water. The method also includes cooling at least a portion of the fermentation feedstock or fermentation broth to solidify at least a portion of the water, and separating at least a portion of the solidified water from the fermentation feedstock or fermentation broth using a solid-liquid phase separation.

The method may also include pre-processing of the fermentation feedstock and/or fermentation broth prior to phase separation.

The method may further include combining ammonia absorption refrigeration with separating at least a portion of the solidified water from the fermentation feedstock or fermentation broth.

In certain embodiments, the method may include separating broth particulates from the fermentation feedstock and/or fermentation broth before cooling at least a portion of the fermentation feedstock or fermentation broth and separating at least a portion of the solidified water from the fermentation feedstock or fermentation broth.

The fermentation feedstock or fermentation broth may include water, alcohol, ethanol, propanol, butanol, organic acids, acetic acid, acetate, sodium acetate, calcium acetate, lactic acid, sodium lactate, calcium lactate, inorganic acids, sulfuric acid, nitric acid, aldehydes, furfural, 5-hydroxymethyl furfural, lignin, acid-soluble lignin, and/or acid-insoluble lignin.

The fermentation broth may include about 5 volume percent ethanol before separating at least a portion of the solidified water from the fermentation feedstock or fermentation broth, and the fermentation broth may include at least about 15 volume percent ethanol after separating at least a portion of the solidified water from the fermentation feedstock or fermentation broth.

The method may also include dehydrating the ethanol after separating at least a portion of the solidified water from the fermentation feedstock or fermentation broth to produce motor-grade fuel ethanol.

The method may further include melting at least a portion of the solidified water for heat integration value.

In certain embodiments, consuming at least a portion of a lignocellulosic fermentation feedstock comprises exothermic processes to produce heat. In these embodiments, at least a portion of the heat may be removed from the consuming step, and at least a portion of the heat may be used to drive a chilling process used in the cooling step.

The method may also include distillation, wherein the heat of cooling is at least partially integrated with the heat of distillation.

The lignocellulose may include energy cane, sugar cane, miscanthus, napiergrass, municipal solid waste, paper mill residue, forest litter, corn stover, and/or agricultural residues.

The fermentation feedstock may include 5-carbon sugars, 6-carbon sugars, and/or 12-carbon sugars.

The method may also include pretreating the feedstock using at least a portion of a heat integration fluid.

According to some embodiments, a method of producing a biofuel component may be achieved by consuming at least a portion of a sugar fermentation feedstock with a fermentation organism to produce butanol in fermentation broth, the fermentation feedstock and fermentation broth comprising water and other components. The method also includes cooling at least a portion of the fermentation feedstock or fermentation broth to solidify at least a portion of the water, and separating at least a portion of the solidified water from the fermentation feedstock or fermentation broth using a solid-liquid phase separation. In certain embodiments, the butanol may include isobutanol.

The method may further include solidifying at least a portion of the other components. The other components may include organic acids, acetic acid, acetate, sodium acetate, calcium acetate, lactic acid, sodium lactate, calcium lactate, inorganic acids, sulfuric acid, nitric acid, aldehydes, furfural, 5-hydroxymethyl furfural, lignin, acid-soluble lignin, and/or acid-insoluble lignin.

In certain embodiments, the steps of cooling at least a portion of the fermentation feedstock or fermentation broth and separating at least a portion of the solidified water from the fermentation feedstock or fermentation broth may occur using a side stream during the step of consuming at least a portion of the sugar fermentation feedstock.

The method may also include pre-processing the fermentation feedstock and/or fermentation broth prior to phase separation.

The method may further include combining ammonia absorption refrigeration with separating at least a portion of the solidified water from the fermentation feedstock or fermentation broth.

The method may further include separating broth particulates from the fermentation broth before the steps of cooling at least a portion of the fermentation feedstock or fermentation broth and separating at least a portion of the solidified water from the fermentation feedstock or fermentation broth.

The method may also include the step of returning at least a portion of the broth particulates to the step of consuming at least a portion of the sugar fermentation feedstock.

The method may also include melting at least a portion of the ice crystals to form water and returning at least a portion of the water to an earlier process step. For example, the earlier process step may include the step of feedstock preparation, or the step of consuming at least a portion of the sugar fermentation feedstock.

In certain embodiments, the step of consuming at least a portion of the sugar fermentation feedstock may include exothermic processes to produce heat. For example, the method may also include removing at least a portion of the heat from the step of consuming at least a portion of the sugar fermentation feedstock, and using the heat to drive a chilling process used in the step of cooling at least a portion of the fermentation feedstock or fermentation broth.

The sugar feedstock may include lignocellulosic feedstocks, cereal feedstocks, grain feedstocks, sugar cane feedstocks, and/or energy cane feedstocks.

The step of separating at least a portion of the solidified water from the fermentation feedstock or fermentation broth may include a liquid-liquid separation.

The phase separation may include freeze-concentration and distillation. In certain embodiments, the heat of freeze-concentration may be at least partially integrated with the heat of distillation.

The fermentation broth may include about 2 volume percent butanol before separating at least a portion of the solidified water from the fermentation feedstock or fermentation broth, and the fermentation broth may include at least about 6 volume percent butanol after separating at least a portion of the solidified water from the fermentation feedstock or fermentation broth.

According to some embodiments, the invention may be directed to a biofuel made according to any of the methods described herein.

According to some embodiments, a biofuel component may include a biologically-derived carbohydrate material separated from a quantity of water by fractional freezing methods. The biologically-derived carbohydrate material may include an alcohol, such as ethanol or butanol. The water may include a fermentation broth and/or a fermentation feedstock. The biologically-derived carbohydrate material may be produced, at least in part, by a microorganism within a period of less than about five years, as opposed to materials that evolve through natural occurrences over extended periods of time, namely more than about five years.

According to some embodiments, a system for producing a biofuel may include a fermentation vessel adapted to contain a biological organism; a first heat removal device in fluid communication with the fermentation vessel, and adapted to reduce a temperature of a substance to solidify at least one component of the substance; and a solid-liquid separation device in fluid communication with the fermentation vessel and/or the first heat removal device, and adapted to separate a solid portion from a liquid portion.

The system may also include a second heat removal device in fluid communication with the fermentation vessel, and adapted to reduce a temperature of a substance to at least remove a heat of fermentation; and a chilling device adapted to receive at least a portion of the heat removed by the second heat removal device and provide cooling to the first heat removal device.

In certain embodiments, the system may also include a distillation device in fluid communication with the fermentation vessel and adapted to separate one or more components of a fermentation broth; a second heat removal device in fluid communication with the distillation device, and adapted to reduce a temperature of a substance; and a chilling device adapted to receive at least a portion of the heat removed by the second heat removal device and provide cooling to the first heat removal device.

The system may also include a melting device in fluid communication with the first heat removal device, and adapted to liquefy at least a portion of material separated in the solid-liquid separation device.

The system may further include a biomass separation device in fluid communication with the fermentation vessel and the first heat removal device, and adapted to separate at least a portion of biomass from a fermentation broth.

According to some embodiments, a system for producing a biofuel may include a vessel adapted to contain a fermentation feedstock; a first heat removal device in fluid communication with the vessel, and adapted to reduce a temperature of a substance to solidify at least one component of the substance; and a solid-liquid separation device in fluid communication with the vessel and/or the first heat removal device, and adapted to separate a solid portion from a liquid portion.

According to some embodiments, the invention may be directed to a biofuel made using any of the systems described herein.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention. In the drawings.

DETAILED DESCRIPTION

Figure 1:
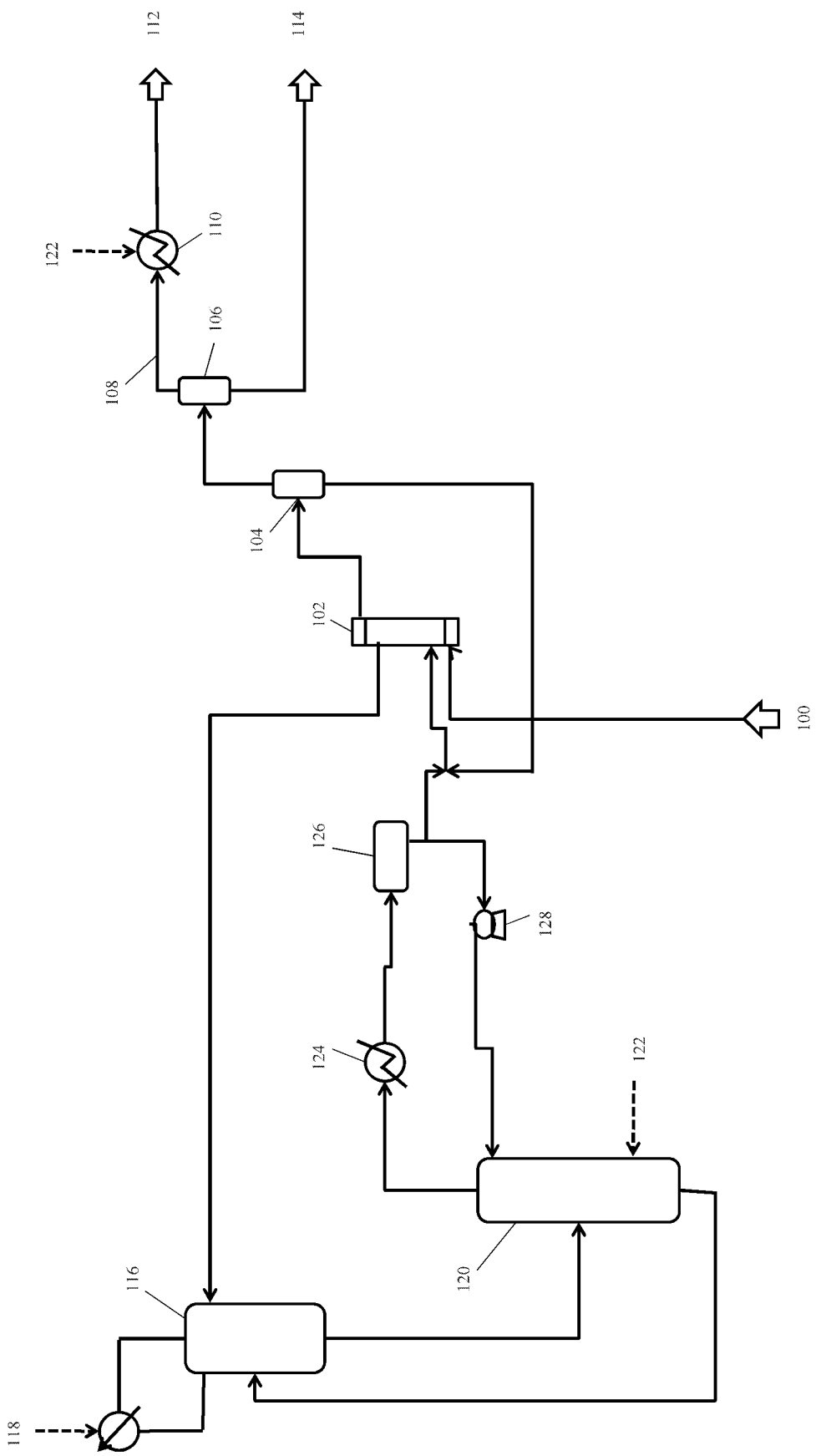
FIG. 1 is a process flow diagram for freeze concentration of an ethanol-water mixture.

The invention is directed to methods and systems for producing biofuels and other renewable materials using phase separations, such as fractional freezing or crystallization, as well as biofuel component compositions made according to such methods.

As used herein, the term "renewable material" preferably refers to a substance and/or an item that has been at least partially derived from a source and/or a process capable of being replaced at least in part by natural ecological cycles and/or resources. Renewable materials may broadly include, for example, chemicals, chemical intermediates, solvents, adhesives, lubricants, monomers, oligomers, polymers, biofuels, biofuel intermediates, biogasoline, biogasoline blendstocks, biodiesel, green diesel, renewable diesel, biodiesel blend stocks, biodistillates, biochar, biocoke, renewable building materials, and/or the like. In certain embodiments, the renewable material may include one or more biofuel components. For example, the renewable material may include an alcohol, such as ethanol, butanol, or isobutanol, or lipids.

The term "biofuel" preferably refers to components and/or streams suitable for use as a fuel and/or a combustion source derived at least in part from renewable sources. The biofuel can be sustainably produced and/or have reduced and/or no net carbon emissions to the atmosphere, such as when compared to fossil fuels. According to some embodiments, renewable sources can exclude materials mined or drilled, such as from the underground. In some embodiments, renewable resources can include single cell organisms, multi-cell organisms, plants, fungi, bacteria, algae, cultivated crops, non-cultivated crops, timber, and/or the like. Biofuels can be suitable for use as transportation fuels, such as for use in land vehicles, marine vehicles, aviation vehicles, and/or the like. More particularly, the biofuels may include gasoline, diesel, jet fuel, kerosene, and/or the like. Biofuels can be suitable for use in power generation, such as raising steam, exchanging energy with a suitable heat transfer media, generating syngas, generating hydrogen, making electricity, and/or the like.

The term "solidify," as used herein, preferably refers to changing a liquid or gaseous substance into a solid form, which includes crystallizing and condensing. An example of a two-part crystallization process is provided in U.S. Pat. No. 3,177,265, issued to Lammers on Apr. 6, 1965, the relevant portions of which are incorporated herein by reference. Standard MSMPR (mixed suspension-mixed product removal) crystallizers are available from Swenson Technology, Inc. of Monee, Ill.

As discussed in greater detail below, methods for reducing energy consumption in ethanol purification processes may involve removing some water by crystallization. For example, an ethanol-water mixture that results after fermentation in a lignocellulosic ethanol process or other sugar-to-fuel ethanol processes may be freeze concentrated. Alternatively, it may be worthwhile to freeze-concentrate a hydrolyzate solution prior to fermentation when used in conjunction with fermenting organisms that have high tolerance to ethanol. Freeze-concentration or freeze-crystallization includes cooling the fermentation broth such that water preferentially solidifies while the renewable material remains substantially in the liquid phase.

Hydrolyzate preferably broadly refers to a substance produced by hydrolysis.

Lignocellulosic preferably broadly refers to materials containing cellulose, hemicellulose, lignin, and/or the like, such as may be derived from plant material and/or the like. Lignocellulosic material may include any suitable material, such as sugar cane, sugar cane bagasse, energy cane bagasse, rice, rice straw, corn, corn stover, wheat, wheat straw, maize, maize stover, sorghum, sorghum stover, sweet sorghum, sweet sorghum stover, cotton remnant, sugar beet, sugar beet pulp, soybean, rapeseed, jatropha, switchgrass, miscanthus, other grasses, cacti, timber, softwood, hardwood, wood waste, sawdust, paper, paper waste, agricultural waste, municipal waste, any other suitable biomass material, and/or the like.

Lignin preferably broadly refers to a biopolymer that may be part of secondary cell walls in plants, such as a complex highly cross-linked aromatic polymer that may covalently link to hemicellulose.

Hemicellulose preferably broadly refers to a branched sugar polymer composed mostly of pentoses, such as with a generally random amorphous structure and typically may include up to hundreds of thousands of pentose units.

Cellulose preferably broadly refers to an organic compound with the formula $(C_6H_{10}O_5)_z$ where z includes any suitable integer. Cellulose may include a polysaccharide with a linear chain of several hundred to over ten thousand hexose units and a high degree of crystalline structure, for example.

According to some embodiments, a method of producing a renewable material may be achieved by consuming at least a portion of a fermentation feedstock with a fermentation organism to produce a renewable material in fermentation broth, the fermentation feedstock and fermentation broth comprising water. The method also includes separating at least a portion of the water from the fermentation feedstock or fermentation broth using one or more phase separations. The phase separations may include a solid-liquid separation, a liquid-liquid separation, a vapor-liquid separation, both a solid-liquid separation and a liquid-liquid separation, both a vapor-liquid separation and a liquid-liquid separation, or even distillation.

The fermentation feedstock may include carbohydrates, sugars derived at least in part from polysaccharides, sugar monomers, sugar dimers, sugar oligomers, sugars, sugars derived at least in part from plant cell walls, and/or sugars derived at least in part from storage polysaccharides. The term "storage polysaccharides," as used herein, preferably includes starch.

The method may further include crystallizing one or more components of the fermentation feedstock and/or fermentation broth. Such components may include water, alcohol, ethanol, propanol, butanol, organic acids, acetic acid, acetate, sodium acetate, calcium acetate, lactic acid, sodium lactate, calcium lactate, inorganic acids, sulfuric acid, nitric acid, aldehydes, furfural, 5-hydroxymethyl furfural, lignin, acid-soluble lignin, and/or acid-insoluble lignin.

Fluidized bed heat exchangers may be used to carry out the crystallization. One example of a commercially available fluidized bed heat exchanger is the APEX 2000, available from Advanced Heat Transfer Technologies of The Woodlands, Tex. The APEX 2000 is a single-pass, vertical shell and tube heat exchanger, in which solid particles are kept in a quasi-fluidized state by maintaining fluidization velocities in the liquid within the tubes. The fluidized bed heat exchanger can heat, cool, or concentrate liquids that cause fouling of heat transfer surfaces in conventional heat exchangers.

A fluidized bed heat exchanger may operate as follows: a severe fouling liquid is supplied to the inlet channel at the base of the heat exchanger where a flow distribution system provides uniform distribution of liquid and particles throughout the internal tube-side surface of the tube bundle. The solid particles, which are maintained in a fluidized state, exert a polishing or scouring effect on the tube walls. Continuous agitation of the liquid boundary layer adjacent to the tube wall results in high levels of turbulence and non-declining heat transfer coefficients at relatively low velocities. The scouring action at the tube wall removes tube-side deposits at an early stage, which are then discharged through the outlet channel. The particles are disengaged from the liquid after a significant velocity reduction in the outlet channel and returned to the inlet channel through one or more downcomer tubes where the cycle is repeated.

In certain embodiments, the method may include solidifying the water, such as by forming ice. For example, the method may include removing enthalpy from the fermentation feedstock and/or fermentation broth, such as through an endothermic reaction, namely cooling. In particular, the method may include lowering a temperature of the fermentation feedstock and/or the fermentation broth below an incipient crystallization temperature, or below a binary eutectic point, or below a ternary eutectic point, or below a quaternary eutectic point.

According to some embodiments, the method may include adding enthalpy to the fermentation feedstock and/or fermentation broth, namely heating. For example, the method may include raising a temperature of the fermentation feedstock and/or the fermentation broth, for example to or above a boiling point of the renewable material and generating a vapor enriched in renewable material. As another example, the method may include lowering a pressure of the fermentation feedstock and/or the fermentation broth to or below the saturation pressure of the fermentation broth and generating a vapor enriched in renewable material. Additionally, the vapor may be condensed to form two liquid phases. A first liquid phase may be substantially at the solubility limit of water in the renewable material, while a second liquid phase may be substantially at the solubility limit of the renewable material in water. The two liquid phases may be separated, whereupon the first liquid phase may be returned to the step of generating the vapor enriched in renewable material. The method may further include generating a second vapor from the second liquid phase. Generation of the second vapor may occur at a reduced pressure. Furthermore, heat that is at least partially derived from condensing the first vapor may be used to generate the second vapor. Examples 2-7 below illustrate the use of evaporators for concentrating isobutanol.

In certain embodiments, the method may include pre-processing the fermentation feedstock and/or fermentation broth prior to phase separation. Pre-processing may include solid/liquid contaminant removal, micro-organism removal, particulate removal, dissolved oxygen removal, dissolved nitrogen removal, dissolved carbon dioxide removal, dissolved solids removal, and the like.

The method may also include separating broth particulates from the fermentation feedstock and/or fermentation broth. As used herein, the term "broth particulates" preferably includes biological organisms.

The step of separating at least a portion of the water from the fermentation feedstock or fermentation broth may occur in a single stage or in multiple stages, and may include such techniques as fractional freezing and/or re-slurrying. As used herein, the term "fractional freezing" preferably refers to enriching a solution by partially freezing water and removing frozen material that is poorer in the dissolved material than is the liquid portion left behind, while the term "re-slurrying" preferably refers to purifying dissolved material from the frozen water by recontacting with liquid solution. Additionally, actual separation of formed solids may occur in multiple stages, possibly interleaved with multiple cooling stages. For example, the fermentation feedstock or fermentation broth may be cooled, in one or more steps, to a first reduced temperature, such as between about 0 and about −20° C. Any solids that are formed can be separated off, and then further cooling, in one or more steps, may be carried out to a second temperature, such as between about −20 and about −40° C., with any further solids being separated off. Depending on the composition of the starting liquid, the two or more separate solids compositions may be different from one another. Any of these separation steps may occur substantially simultaneously with at least a portion of, or substantially after, the step of consuming at least a portion of the fermentation feedstock.

The step of consuming at least a portion of the fermentation feedstock may occur under batch fermentation, under fed-batch fermentation, under continuous fermentation, or under semi-continuous fermentation.

Similarly, the step of separating at least a portion of the water from the fermentation feedstock or fermentation broth may occur under batch operation, under fed-batch operation, under continuous operation, or under semi-continuous operation.

The phase separation of this method may include freeze-concentration and distillation, with the heat of freeze-concentration at least partially integrated with the heat of distillation.

Separating at least a portion of the water from the fermentation feedstock or fermentation broth may occur at a temperature from about 0° C. to about −100° C., such as at about −20° C. Furthermore, this step may occur above atmospheric pressure, or substantially at atmospheric pressure, or below atmospheric pressure.

Various techniques or devices may be used to separate at least a portion of the water from the fermentation feedstock or fermentation broth, such as using rotating equipment, a centrifuge, a filtering device, gravity sedimentation or decantation, or a wash column, or by solidifying the water.

The fermentation organism may include, for example, fungi, bacteria, algae, cyanobacteria, yeast, and/or other similar organisms that produce lipids or fatty acids during fermentation.

Separating at least a portion of the water from the fermentation feedstock or fermentation broth may result in a concentration of renewable material of at least 20%, or at least 3 times the concentration of the fermentation broth.

The method may also include an additional purification step. The additional purification step may result in a concentration of renewable material of at least 95%. Additionally or alternatively, the additional purification step may result in an anhydrous renewable material. The additional purification step may be carried out using molecular sieves, azeotropic distillation, or liquid-liquid extraction, for example.

According to some embodiments, a method of producing a renewable material may be achieved by consuming at least a portion of a fermentation feedstock with a fermentation organism to produce a renewable material in fermentation broth, the fermentation feedstock and fermentation broth each comprising water and originating from opposite ends of a multi-phasic liquid/liquid mixture. These solvents form two-phase solutions with water. When a solution of solvent in water is mixed with a solution of water in solvent, there is the potential to form new liquid/liquid compositions that are advantageous for further downstream processing. The method also includes concentrating at least a portion of the renewable material from the fermentation feedstock or fermentation broth using one or more phase separations. Concentrating the renewable material from the fermentation feedstock or fermentation broth may include a liquid-liquid separation, or both a solid-liquid separation and a liquid-liquid separation.

The fermentation broth may include renewable material at a concentration below a solubility limit of the renewable material in water. In certain embodiments, concentrating the renewable material from the fermentation feedstock or fermentation broth may include mixing the fermentation broth with a second solution, wherein the second solution includes water at a concentration substantially below the solubility limit of water in the renewable material. The method may further include forming two liquid phases. For example, a first liquid phase may be substantially at the solubility limit of water in the renewable material, and a second liquid phase may be substantially at the solubility limit of the renewable material in water. An example of this two-phase solution concept applied to the method of producing a renewable material is described in Example 1 below.

One method of producing a renewable feedstock, according to some embodiments, may include removing at least a portion of water from a feedstock by phase separation prior to fermentation.

According to some embodiments, the invention may be directed to a renewable material made according to any of the methods described herein.

According to some additional embodiments, a method of producing a biofuel component may be achieved by consuming at least a portion of a lignocellulosic fermentation feedstock with a fermentation organism to produce ethanol in fermentation broth, the fermentation feedstock and fermentation broth comprising water. The method also includes cooling at least a portion of the fermentation feedstock or fermentation broth to solidify at least a portion of the water, and separating at least a portion of the solidified water from the fermentation feedstock or fermentation broth using a solid-liquid phase separation.

The method may also include pre-processing of the fermentation feedstock and/or fermentation broth prior to phase separation.

The method may further include combining ammonia absorption refrigeration with separating at least a portion of the solidified water from the fermentation feedstock or fermentation broth.

In certain embodiments, the method may include separating broth particulates from the fermentation feedstock and/or fermentation broth before cooling at least a portion of the fermentation feedstock or fermentation broth and separating at least a portion of the solidified water from the fermentation feedstock or fermentation broth.

The fermentation feedstock or fermentation broth may include, for example, water, alcohol, ethanol, propanol, butanol, organic acids, acetic acid, acetate, sodium acetate, calcium acetate, lactic acid, sodium lactate, calcium lactate, inorganic acids, sulfuric acid, nitric acid, aldehydes, furfural, 5-hydroxymethyl furfural, lignin, acid-soluble lignin, and/or acid-insoluble lignin.

The fermentation broth may include about 5 volume percent ethanol before separating at least a portion of the solidified water from the fermentation feedstock or fermentation broth, and the fermentation broth may include at least about 15 volume percent ethanol after separating at least a portion of the solidified water from the fermentation feedstock or fermentation broth.

The method may also include dehydrating the ethanol after separating at least a portion of the solidified water from the fermentation feedstock or fermentation broth to produce motor-grade fuel ethanol.

The method may further include melting at least a portion of the solidified water for heat integration value.

In certain embodiments, consuming at least a portion of a lignocellulosic fermentation feedstock comprises exothermic processes to produce heat. In these embodiments, at least a portion of the heat may be removed from the consuming step, and at least a portion of the heat may be used to drive a chilling process used in the cooling step.

The method may also include distillation, wherein the heat of cooling is at least partially integrated with the heat of distillation.

The lignocellulose may include energy cane, sugar cane, miscanthus, napiergrass, municipal solid waste, paper mill residue, forest litter, corn stover, and/or agricultural residues.

The fermentation feedstock may include 5-carbon sugars, 6-carbon sugars, and/or 12-carbon sugars.

The method may also include pretreating the feedstock using at least a portion of a heat integration fluid.

In certain embodiments, the separation of water from ethanol uses at least 10 percent less energy than energy consumed using conventional distillation separation. The energy savings may be increased by employing additional heat integration options, such as using the heat from the distillation to drive the cooling water in the distillation tower.

Although a number of combinations of different technologies may be used for producing ice crystals from the fermentation feedstock and/or fermentation broth mixed with water and separating them, one example is illustrated in FIG. 1. While FIG. 1 illustrates an example with an ethanol-water mixture, the process would be applicable for a hydrolyzate mixture as well.

As shown in FIG. 1, an ethanol-water mixture 100 from a fermentation section is cooled in a crystallizer 102, such as a fluidized bed heat exchanger, to give a slurry containing 10-40% ice. Cooling in the crystallizer 102 causes preferential crystallization of water in almost pure form. In the event that a fluidized bed heat exchanger is used for area clean crystallization, the scraping particles used for keeping the heat transfer are removed in a head space shown by 104.

Ice 108 formed in the crystallizer 102 is separated from the ice-water-ethanol slurry using a centrifuge/filter column/wash column/decanter 106 and this ice 108 is melted in a heater 110 to form water to be used in a pretreatment section 112. The ethanol-water mixture which is now enriched in ethanol may be separated in a distillation tower 114 by using some other process to give an azeotropic mixture or pure ethanol.

The refrigeration in the crystallizer 102 may be achieved by using any refrigerant. In a particular case considered here, ammonia absorption refrigeration is used. Liquid ammonia is expanded in the crystallizer 102 and this produces the refrigeration effect required for crystallization of water. The ammonia vapor is then sent over to an absorption tower 116 where it is absorbed into cooling water 118 to form an aqueous $NH_3$ solution. The aqueous solution is then pressurized by ammonia pump 128 and ammonia is sent over to an ammonia fractionation tower 120. Waste heat 122 from the process is used to liberate ammonia from the solution and the ammonia vapors are condensed in an ammonia condenser 124 to give liquid ammonia, which may be stored in an ammonia holding vessel 126 at high pressure which may then be sent to the crystallizer 102. In the ethanol industry there are a number of sources for waste heat. One such source is the process heat required to be removed from the ethanol condenser in the ethanol-water distillation system. Another alternative is the excess low pressure steam that is produced in the process.

As shown in FIG. 1, an ammonia absorption refrigeration system can use waste heat 122 in a lignocellulosic ethanol (or sugar-to-ethanol) process to power the refrigeration system. Effective utilization of the waste heat in the process makes it possible to concentrate the ethanol-water solution before distilling it further. The overall effect of employing this strategy is that the energy usage in the separation process can be reduced by up to 40%.

The aqueous ammonia stream formed by dissolving ammonia in the absorption tower may also be used to pretreat lignocellulosic biomass, before it is pressurized and fractionated. This may eliminate the need for standard dilute acid pretreatment, and may significantly increase both hydrolysis and fermentation yields with only a slight increase in process complexity.

According to some embodiments, a method of producing a biofuel component may be achieved by consuming at least a portion of a sugar fermentation feedstock with a fermentation organism to produce butanol in fermentation broth, the fermentation feedstock and fermentation broth comprising water and other components. The method also includes cooling at least a portion of the fermentation feedstock or fermentation broth to solidify at least a portion of the water, and separating at least a portion of the solidified water from the fermentation feedstock or fermentation broth using a solid-liquid phase separation. In certain embodiments, the butanol may include isobutanol.

The method may further include solidifying at least a portion of the other components, such as when fermentation inhibitors are removed by the phase separation. The other components may include organic acids, acetic acid, acetate, sodium acetate, calcium acetate, lactic acid, sodium lactate, calcium lactate, inorganic acids, sulfuric acid, nitric acid, aldehydes, furfural, 5-hydroxymethyl furfural, lignin, acid-soluble lignin, and/or acid-insoluble lignin.

In certain embodiments, the steps of cooling at least a portion of the fermentation feedstock or fermentation broth and separating at least a portion of the solidified water from the fermentation feedstock or fermentation broth may occur using a side stream during the step of consuming at least a portion of the sugar fermentation feedstock.

The method may also include pre-processing the fermentation feedstock and/or fermentation broth prior to phase separation.

The method may further include combining ammonia absorption refrigeration with separating at least a portion of the solidified water from the fermentation feedstock or fermentation broth.

The method may further include separating broth particulates from the fermentation broth before the steps of cooling at least a portion of the fermentation feedstock or fermentation broth and separating at least a portion of the solidified water from the fermentation feedstock or fermentation broth.

The method may also include the step of returning at least a portion of the broth particulates to the step of consuming at least a portion of the sugar fermentation feedstock.

The method may also include melting at least a portion of the ice crystals to form water and returning at least a portion of the water to an earlier process step. For example, the earlier process step may include the step of feedstock preparation, or the step of consuming at least a portion of the sugar fermentation feedstock.

In certain embodiments, the step of consuming at least a portion of the sugar fermentation feedstock may include exothermic processes to produce heat. For example, the method may also include removing at least a portion of the heat from the step of consuming at least a portion of the sugar fermentation feedstock, and using the heat to drive a chilling process used in the step of cooling at least a portion of the fermentation feedstock or fermentation broth.

The sugar feedstock may include lignocellulosic feedstocks, cereal feedstocks, grain feedstocks, sugar cane feedstocks, and/or energy cane feedstocks.

The step of separating at least a portion of the solidified water from the fermentation feedstock or fermentation broth may include a liquid-liquid separation.

The phase separation may include freeze-concentration and distillation. In certain embodiments, the heat of freeze-concentration may be at least partially integrated with the heat of distillation.

The fermentation broth may include about 2 volume percent butanol before separating at least a portion of the solidified water from the fermentation feedstock or fermentation broth, and the fermentation broth may include at least about 6 volume percent butanol after separating at least a portion of the solidified water from the fermentation feedstock or fermentation broth.

For example, isobutanol can be produced during a fermentation process. More particularly, concentrated isobutanol can be extracted via a fermentation side-stream freeze extraction process in which:

1. A side-stream of isobutanol fermentation broth is frozen so that ice crystals are formed in a scraped surface heat exchanger.
2. Ice water crystals are removed from the side-stream frozen fermentation broth by a separation process leaving a more concentrated isobutanol fermentation broth.
3. The concentrated iso-butanol fermentation broth from the side-stream can be further concentrated by repeating steps 1 and 2.

The separated frozen water is recycled back to the fermentation vessel or to fermentation broth make-up. This reduces the isobutanol alcohol level in the fermentation vessel and allows for further fermentation when additional nutrients are added.

This fractional freezing technique is similar to the process of concentrating fruit juice by removing frozen ice. Fruit juice processors use this technique rather than distillation in order to avoid heat damage that distillation causes. Additionally, freezing requires less energy than boiling. With respect to the production of renewable materials, this method is beneficial in that the removal of toxic isobutanol from the fermentation broth allows for the fermentation organism to further ferment nutrients into isobutanol in either a batch, semi-continuous, or continuous fermentation. Also, isobutanol can be extracted and concentrated from a side-stream of fermentation broth, and removal of ice water from a side stream of fermentation broth allows the isobutanol to be concentrated.

Figure 2:
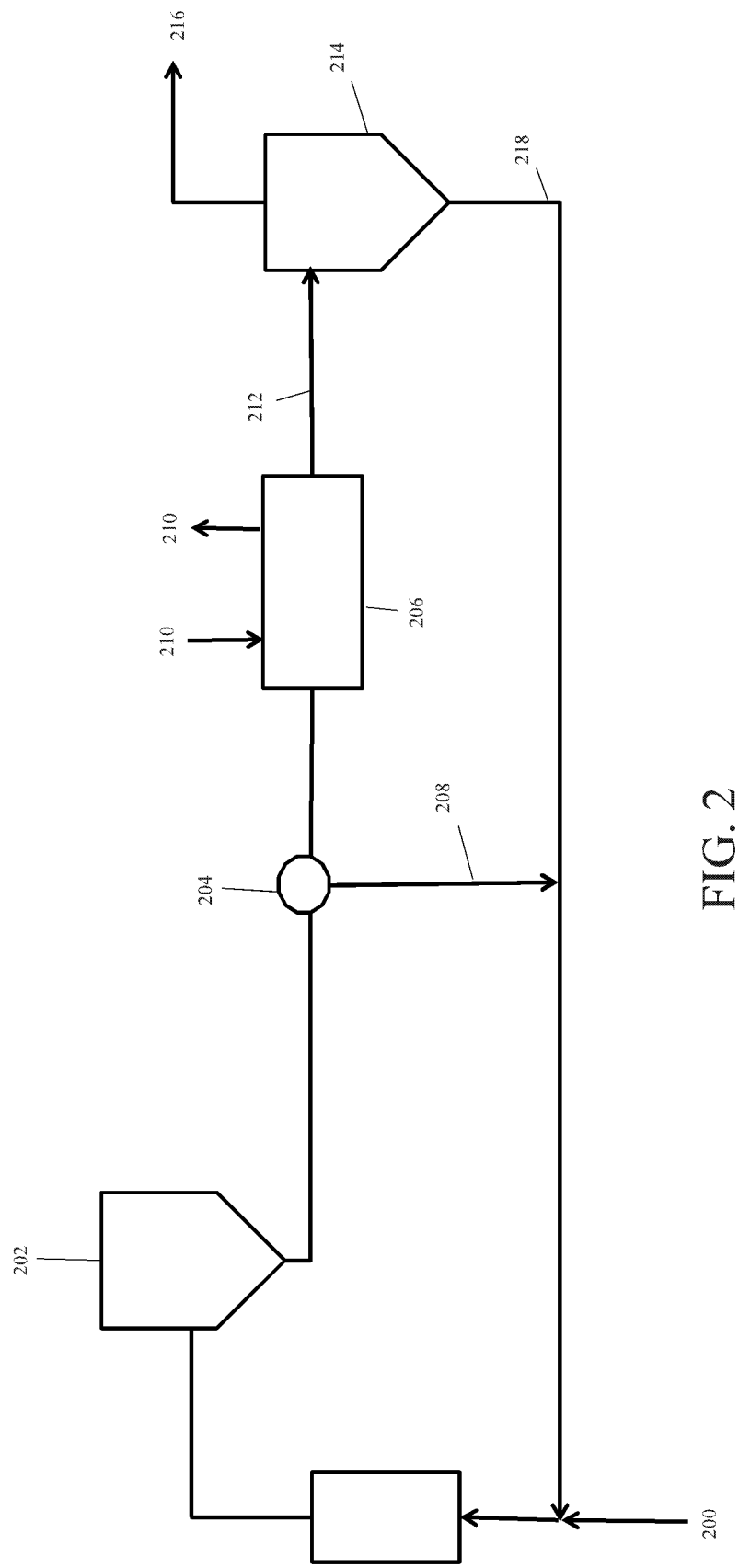
FIG. 2 illustrates a continuous extraction and fermentation process of producing butanol.

FIG. 2 illustrates a continuous extraction and fermentation process of producing butanol. A hot feed of the fermentation feedstock and fermentation broth is fed at about 80° C. to a fermentation section, which cools the mixture to about 40° C. The mixture is then fed to a centrifuge, which separates into approximately 95% fermentation broth, which is fed to a scraped surface heat exchanger, while the remaining 5% yeast recycle is returned to the hot feed. A coolant is circulated through the heat exchanger, and the fermentation broth exits the heat exchanger in the form of ice and liquid butanol, which is separated in a distillation tower at approximately −5° C. to produce pure butanol, while returning a stream of extracted broth to the broth feed.

Figure 3:
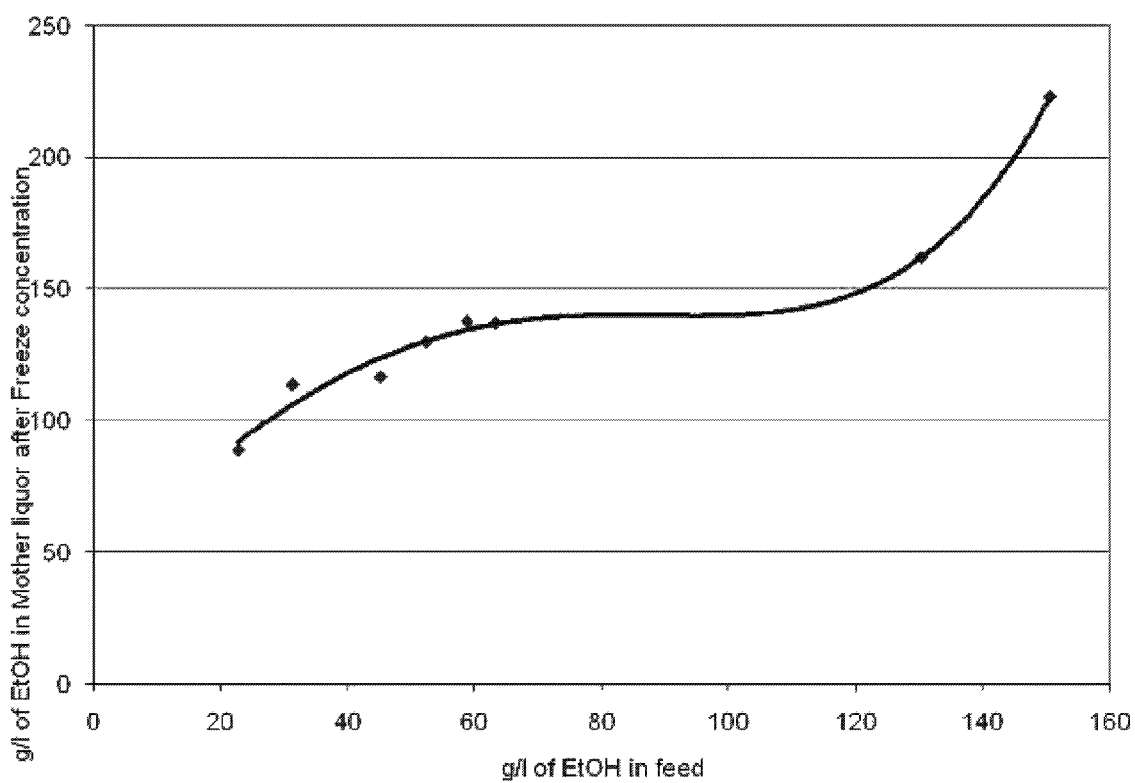
FIG. 3 is a graphical representation of freeze crystallization of ethanol.

When impurities, such as ethanol/organic acids, are present in butanol/water, the butanol is soluble in water up to about 2% by volume at room temperature and atmospheric pressure. With respect to a freezing point curve for the butanol/water, an ice layer, butanol layer, and water-plus-butanol layer will form during freezing. As the freezing proceeds, the remaining liquid will approach the density of the ice. The freeze crystallization characteristics are similar for ethanol, n-butanol, iso-butanol, sec-butanol, acetic acid, and propanol. FIG. 3 is a graphical representation of freeze crystallization of ethanol, with the data gathered at −9° C.

According to some embodiments, the invention may be directed to a biofuel made according to any of the methods described herein.

According to some embodiments, a biofuel component may include a biologically-derived carbohydrate material separated from a quantity of water by fractional freezing methods. The biologically-derived carbohydrate material may include an alcohol, such as ethanol or butanol. The water may include a fermentation broth and/or a fermentation feedstock. The biologically-derived carbohydrate material may be produced, at least in part, by a microorganism within a period of less than about five years, as opposed to materials that evolve through natural occurrences over extended periods of time, namely more than about five years.

According to some embodiments, a system for producing a biofuel may include a fermentation vessel adapted to contain a biological organism; a first heat removal device in fluid communication with the fermentation vessel, and adapted to reduce a temperature of a substance to solidify at least one component of the substance; and a solid-liquid separation device in fluid communication with the fermentation vessel and/or the first heat removal device, and adapted to separate a solid portion from a liquid portion.

The system may also include a second heat removal device in fluid communication with the fermentation vessel, and adapted to reduce a temperature of a substance to at least remove a heat of fermentation; and a chilling device adapted to receive at least a portion of the heat removed by the second heat removal device and provide cooling to the first heat removal device.

In certain embodiments, the system may also include a distillation device in fluid communication with the fermentation vessel and adapted to separate one or more components of a fermentation broth; a second heat removal device in fluid communication with the distillation device, and adapted to reduce a temperature of a substance; and a chilling device adapted to receive at least a portion of the heat removed by the second heat removal device and provide cooling to the first heat removal device.

The system may also include a melting device in fluid communication with the first heat removal device, and adapted to liquefy at least a portion of material separated in the solid-liquid separation device.

The system may further include a biomass separation device in fluid communication with the fermentation vessel and the first heat removal device, and adapted to separate at least a portion of biomass from a fermentation broth.

According to some embodiments, a system for producing a biofuel may include a vessel adapted to contain a fermentation feedstock; a first heat removal device in fluid communication with the vessel, and adapted to reduce a temperature of a substance to solidify at least one component of the substance; and a solid-liquid separation device in fluid communication with the vessel and/or the first heat removal device, and adapted to separate a solid portion from a liquid portion.

According to some embodiments, the invention may be directed to a biofuel made using any of the systems described herein.

Example 1

Figure 4:
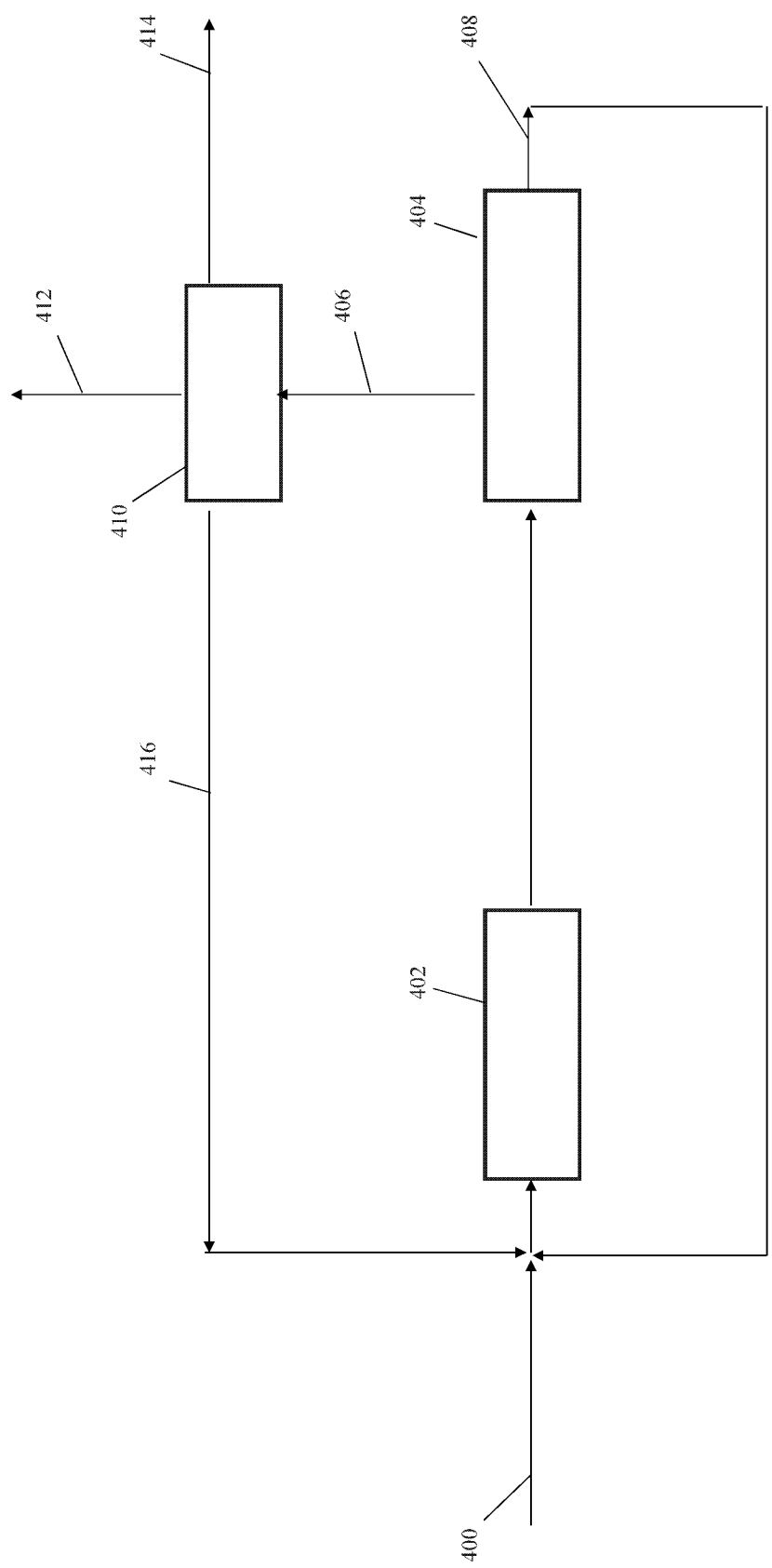
FIG. 4 is a flow-diagram illustrating a method of producing a renewable material using a two-phase solution in Example 1.

As shown in FIG. 4, 1538.7 metric tons of fermentation broth/h (shown at 400) is combined with a solution of 1 wt % bio-based butanol and 99 wt % water at 35° C., and together this mixture is sent to a heat exchanger 402. After exiting the heat exchanger 402, the mixture is cooled to 0° C., whereupon the mixture is still liquid, with 1814.15 metric tons of broth/h in combination with 13 wt % bio-based butanol and 87 wt % water. The mixture is then sent to a decanter 404, and separated into two liquid phases, a first phase 406 of 1674 metric tons of broth/h in combination with 7.4 wt % bio-based butanol and 92.6 wt % water is sent to a phase separation device 410, such as a distillation column, freeze concentration device or multi-effect evaporator, while a second phase 408 of 140 metric tons of broth/h in combination with 80 wt % bio-based butanol and 20 wt % water is sent back to the heat exchanger 402. Upon exiting the phase separation device 410, the first phase 406 is separated into a first stream 412 of 1523 metric tons of water, a second stream 414 of 15 metric tons/h and 100 wt % butanol, and the remainder 416 of 136 metric tons/h in combination with 80 wt % butanol and 20 wt % water is combined with the second phase 408 back at the heat exchanger 402.

Examples 2-6 illustrate the use of evaporators for concentrating isobutanol.

Example 2

Figure 5:
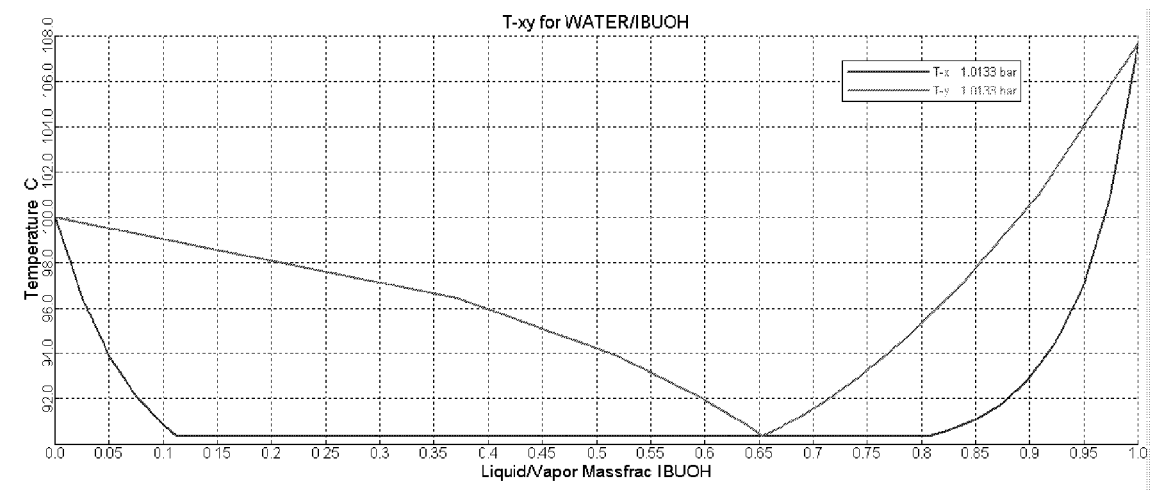
FIGS. 5 and 6 are diagrams illustrating the behavior of an isobutanol-water phase in Example 2.

In this example, the behavior of an isobutanol-water phase is examined. The diagram in FIG. 5 shows the vapor-liquid phase equilibrium relationship for isobutanol and water at atmospheric pressure. The upper line shows the dew point temperature of vapor, and the lower line shows the bubble point temperature of liquid, as a function of mass fraction of isobutanol.

There are several observations to note in FIG. 5:
1. The left and right axes, the bubble at dew point curves intersect at the normal boiling points of the pure components (100° C. and 107.7° C. for water and isobutanol respectively).
2. There is a liquid immiscibility region from approximately 11% isobutanol to approximately 81% isobutanol. The bubble point for any liquid in the immiscible region is equal to the boiling point of the azeotrope, which is 90.4° C.
3. The effect of evaporating and condensing any liquid mixture can be determined from this chart. For example, it can be seen that liquid containing 5 wt % isobutanol will boil at 94° C. The vapor in equilibrium with this must condense at 94° C. and must therefore contain about 51% isobutanol.
4. Consequently, the evaporate from any dilute isobutanol solution containing more than approximately 0.5 wt % isobutanol will, when recondensed, fall into the two-phase region. The relative amounts of each of the two phases produced will vary depending on the original isobutanol concentration, but not the compositions.

Figure 6:
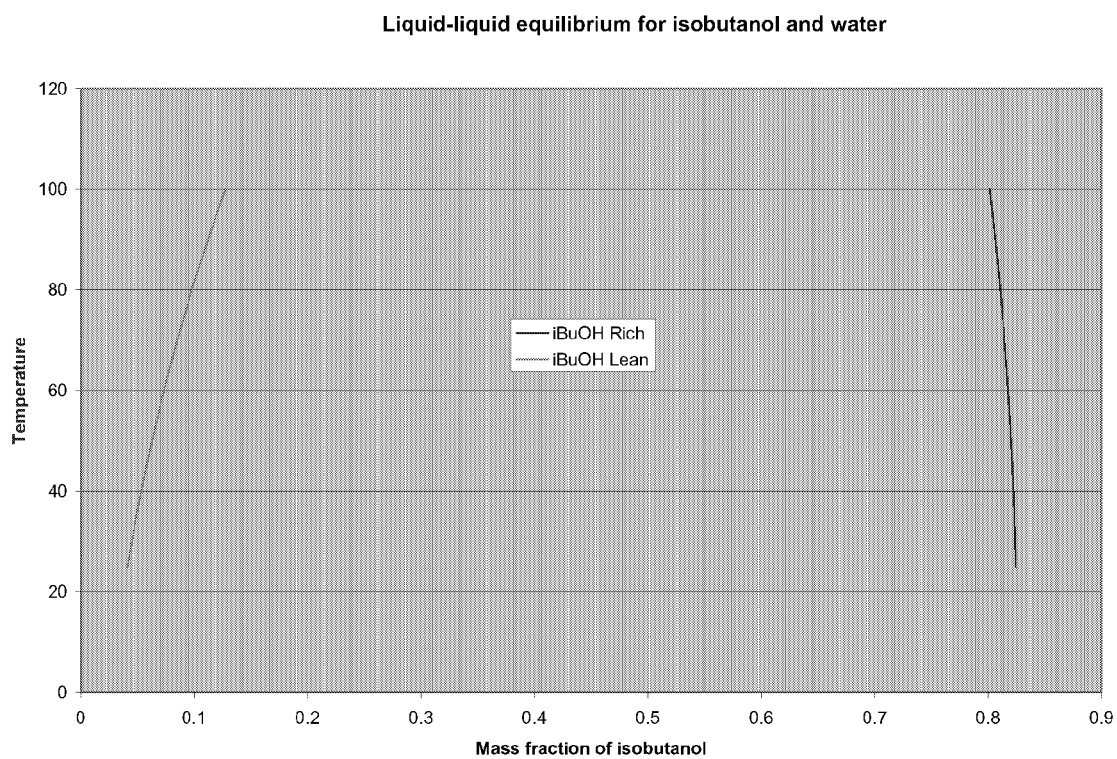

It is also useful to note that the immiscible region becomes larger as the temperature is decreased, as shown in FIG. 6. More particularly, FIG. 6 shows the liquid immiscible region expanding from 11-81% isobutanol at 90.4° C. to 5.3-82% isobutanol at 40° C. Thus at reduced pressure, an even lower isobutanol concentration feed can give a vapor which can be condensed in the immiscible liquid region.

The following examples use the behavior displayed in the present example to show how isobutanol can be extracted from relatively dilute (1-2 wt %) solutions using relatively small amounts of low grade energy.

Example 3

In this example, multiple effect evaporators are examined. Multiple effect evaporators are commonly used in the specialty chemicals industry to evaporate a volatile solvent from an involatile solute. They provide an effective means of heat integration by essentially using the same heat several times by dropping the pressure of the solute.

Figure 7:
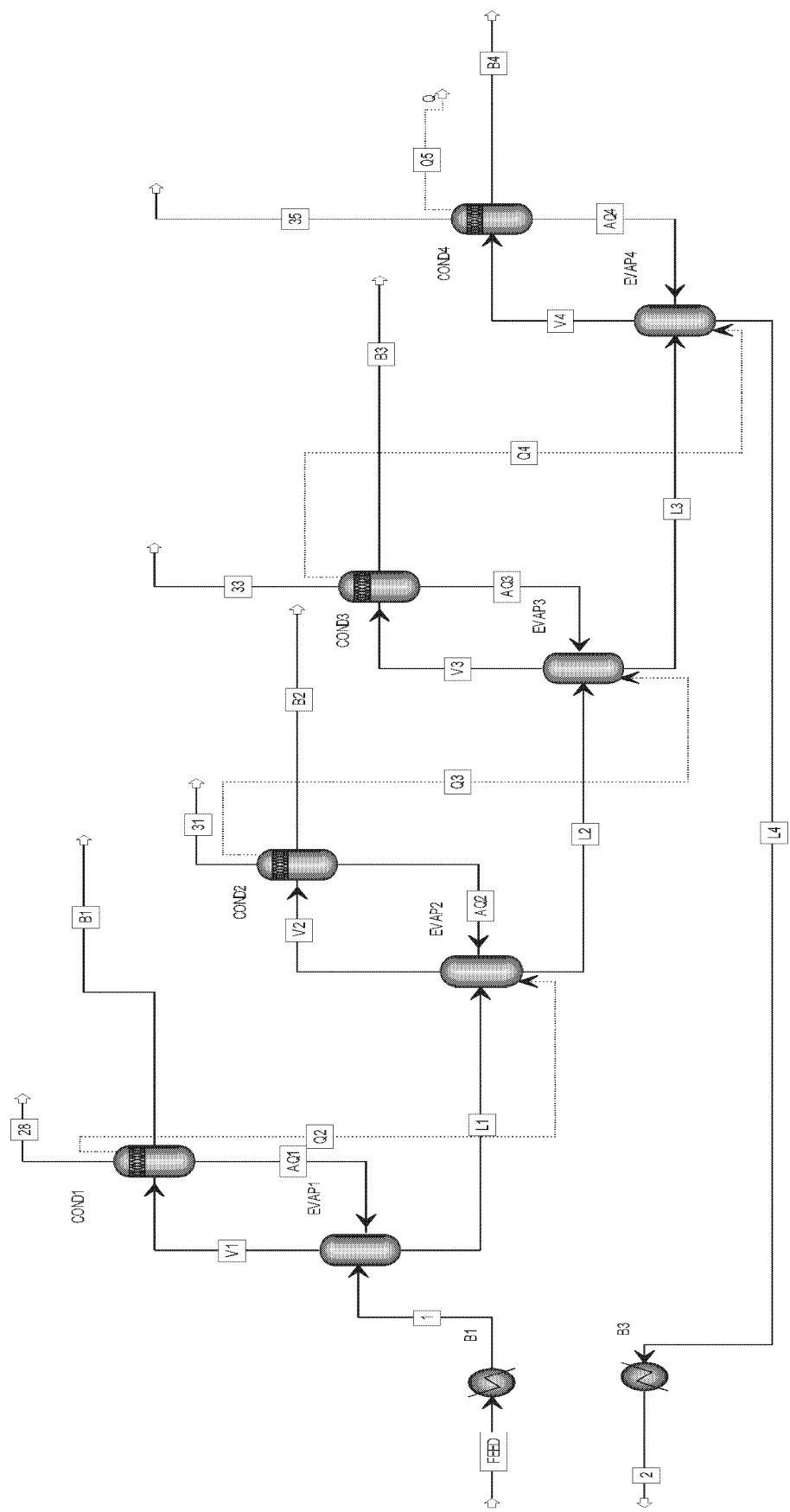
FIG. 7 is a flowsheet illustrating multiple effect evaporators in Example 3.

The case of an isobutanol solution at 1.8 wt % is fed to the flowsheet shown in FIG. 7. The solution is first heated to its dew point at atmospheric pressure and fed to an evaporator (EVAP1). The vapor is condensed in the condenser (COND1), a decanter is used to separate the two liquid phases, and the aqueous phase is returned to the evaporator. The organic phase (labeled B1 in FIG. 7) contains just over 80% isobutanol.

The key trick is that the liquid from the evaporator is then flashed to a second evaporator at a lower pressure, such that it can re-use the heat from the first condenser. In this case, the second evaporator operates at 0.61 bar and 85.4° C. The same process can be repeated for a third stage (0.36 bar and 73° C.) and fourth stage (0.22 bar and 61.7° C.).

Limits to the process include:
1. The preheat required at the first stage, raising the original solution to its bubble point, can be very significant. This can be partially offset by recovering some heat from the liquid leaving the final condenser, and significantly reduced by reducing the pressure at which the first evaporator stage is operated.
2. The pressure of the final evaporator stage is set by the temperature at which cooling water is available. If cooling water is available at 40° C., then the final stage could be operated at a pressure giving a bubble point of 45° C.

Thus, the concept allows extraction of a stream of 80 wt % isobutanol from a large flow of dilute isobutanol, leaving a "raffinate" flow of very dilute (0.5 wt % or less) isobutanol which could be returned to the fermentation reactor.

The optimization of such a design is, however, complex, with many variables available, including (i) the number of evaporator stages ("effects") used, (ii) the amount of vaporization in the first stage, and (iii) the pressure used in the first stage.

There are also two ways in which a series of evaporators could be used as an in situ product removal system for an isobutanol fermentation.
1. If the fermentation broth can be withdrawn from the fermenter leaving the growing cells behind, for example using centrifugation or filtration, then a relatively warm first stage could be used, with a final stage condensed against cooling water.
2. Alternatively, the whole broth could be withdrawn from the fermenter and processed in a series of stages at vacuum, with the final stage condensed against a refrigerant just above 0° C. (to avoid freezing). This may also be used to provide cooling for the (exothermic) fermentation process, but does require that the organism used for fermentation is tolerant of cold conditions.

Example 4

Figure 8:
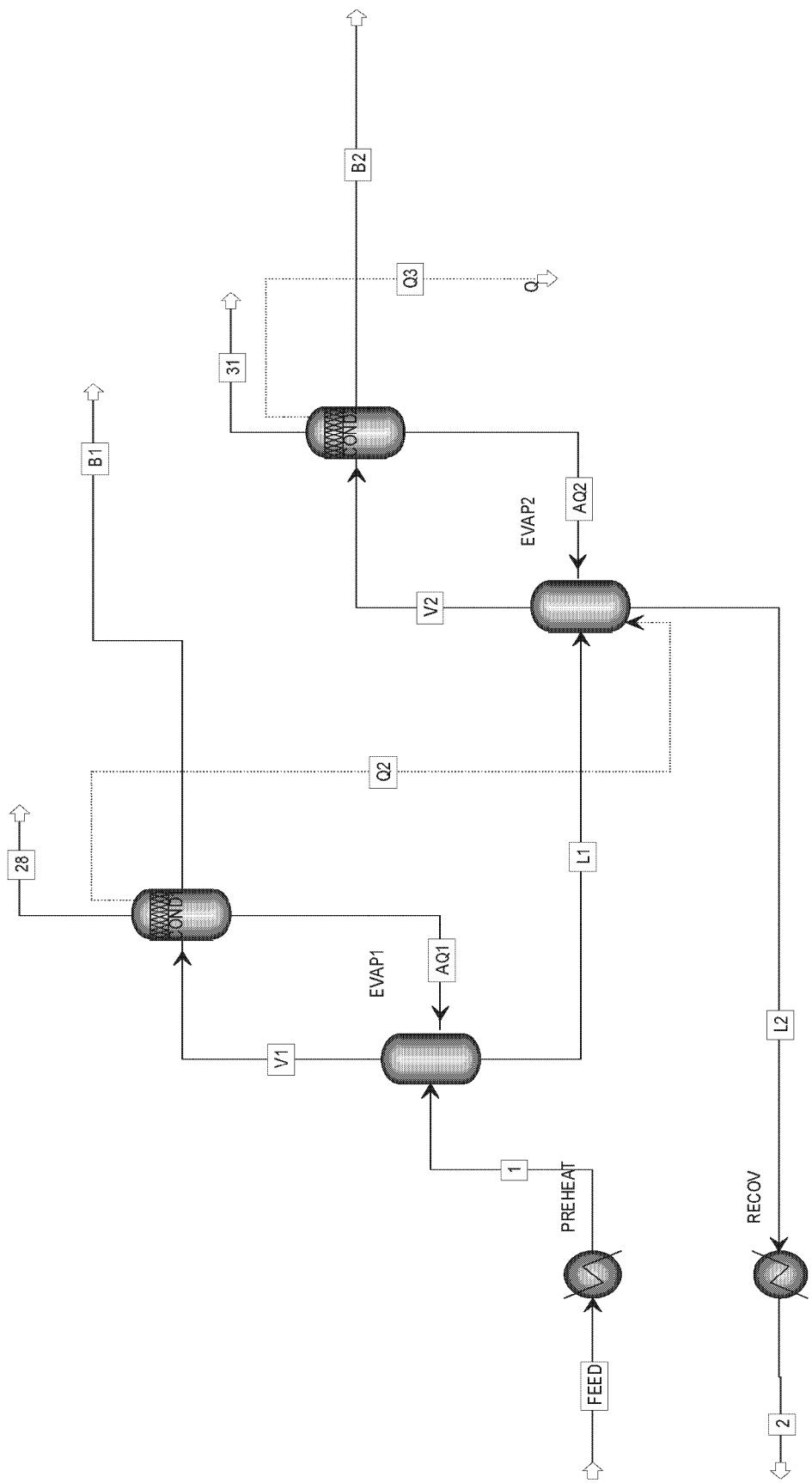
FIG. 8 is a flowsheet illustrating a two-effect system in Example 4.

In this example, a simple two-effect system is examined for cooling water. The simplest useful circuit assumes a two-effect evaporator and has the flowsheet shown in FIG. 8.

An AspenPlus™ simulation was used to optimize the configuration on the basis of isobutanol removal per unit heat used, requiring that the final stage condenser must be at 45° C. At the optimum conditions, the first stage pressure is approximately 0.21 bar, the second stage 0.13 bar, and 1.1% of the total liquid is evaporated in the first stage. For such a process, 51.55% of the isobutanol in the feed is removed from the broth per pass, the preheat consumes 24.5 MW of heat (of which 11.4 MW can be recovered from the lean isobutanol return) and the evaporator consumes 6.5 MW of heat. Thus the energy consumption is approximately 9 MJ/te of isobutanol recovered, the energy being low grade heat—probably LP steam. Note that this does not include the energy required for centrifugation and filtering, pumping costs, or distillation of the 80% isobutanol stream; if the centrifugation or filtering costs are high, it may be preferable to use more energy to recover butanol from the dilute steam (70-80% can be achieved).

Example 5

In this example, a simple two-effect system is examined for a refrigerative system. The refrigerative system has essentially the same flowsheet as in FIG. 8 used in the example above, but operates considerably colder. In the example simulated, the broth (initially at 32° C.) is flashed down to 0.017 bar in the first stage, which causes significant evaporation of isobutanol and water without the application of additional heat. The heat of condensation is used to supplement evaporation in the second stage at 0.01 bar. The vapor is condensed at 5° C. against a suitable refrigerant. This flowsheet recovers about 75% of the isobutanol in the feed as a stream containing 82.5 wt % isobutanol.

The duty of the second condenser is approximately 23 MW, which would require around 6 MW of compression work to deliver. However, it should be noted that there is an option to return the raffinate (which is produced) at 7° C. to the fermenter without fully reheating, so there would be no need for a separate chiller system for the fermenters. It may also be possible to recover "coldness" into the refrigeration system from the cold raffinate return, significantly reducing the refrigeration compression duty.

This option therefore requires about 7.2 MJ of compression work per ton of isobutanol recovered (excluding the final isobutanol distillation and pumping duties).

Example 6

Figure 9:
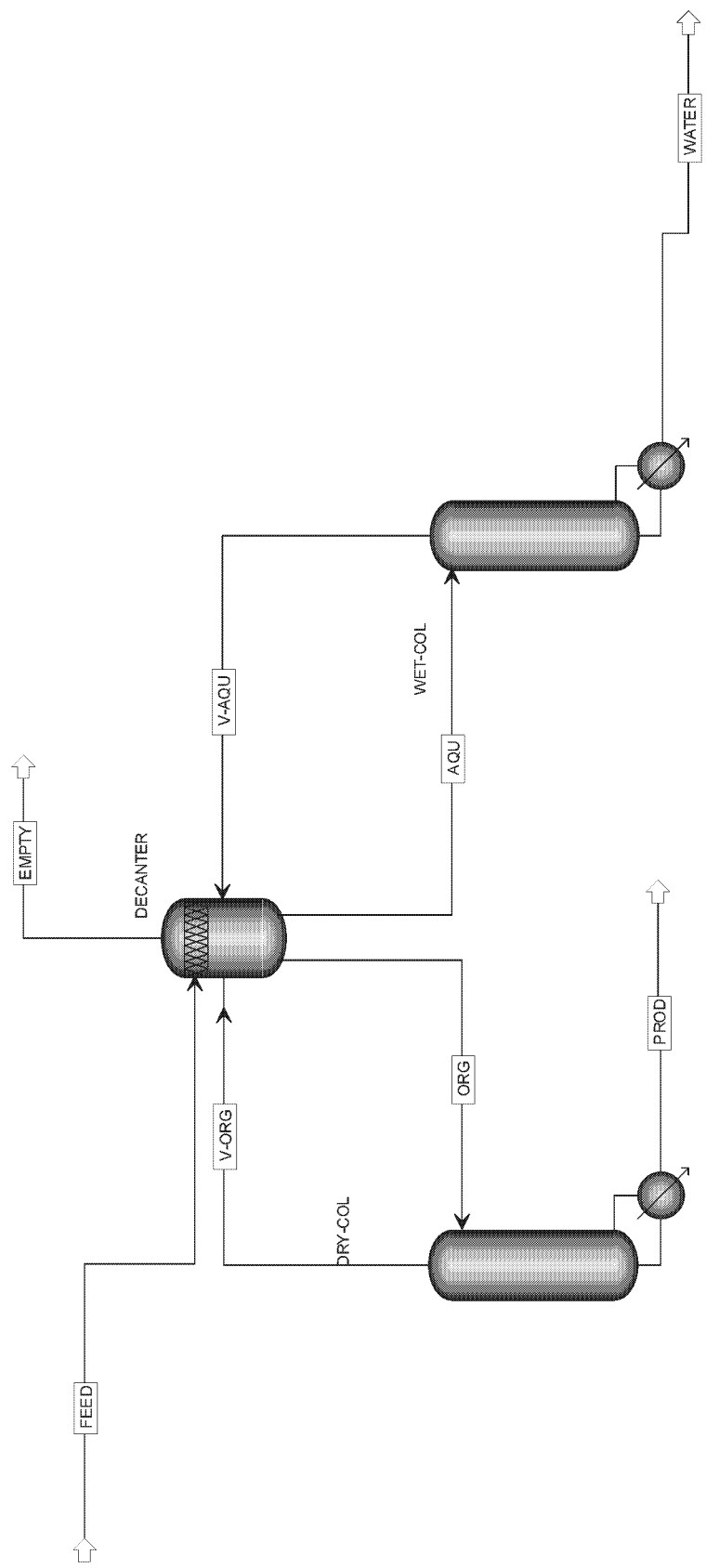
FIG. 9 is a flowsheet illustrating isobutanol polishing distillation in Example 6.

In this example, isobutanol polishing distillation is examined. A standard flowsheet for purifying a mixture with a heterogeneous azeotrope is shown in FIG. 9. Two columns are used: a "dry" column and a "wet" column, with a shared condenser and decanter, into which the feed can be supplied. The two columns purify the isobutanol and the water respectively. The energy use of this system is approximately 1.6 MJ of relatively low grade heat (typically LP steam) per ton of isobutanol product.

Example 7

Figure 10:
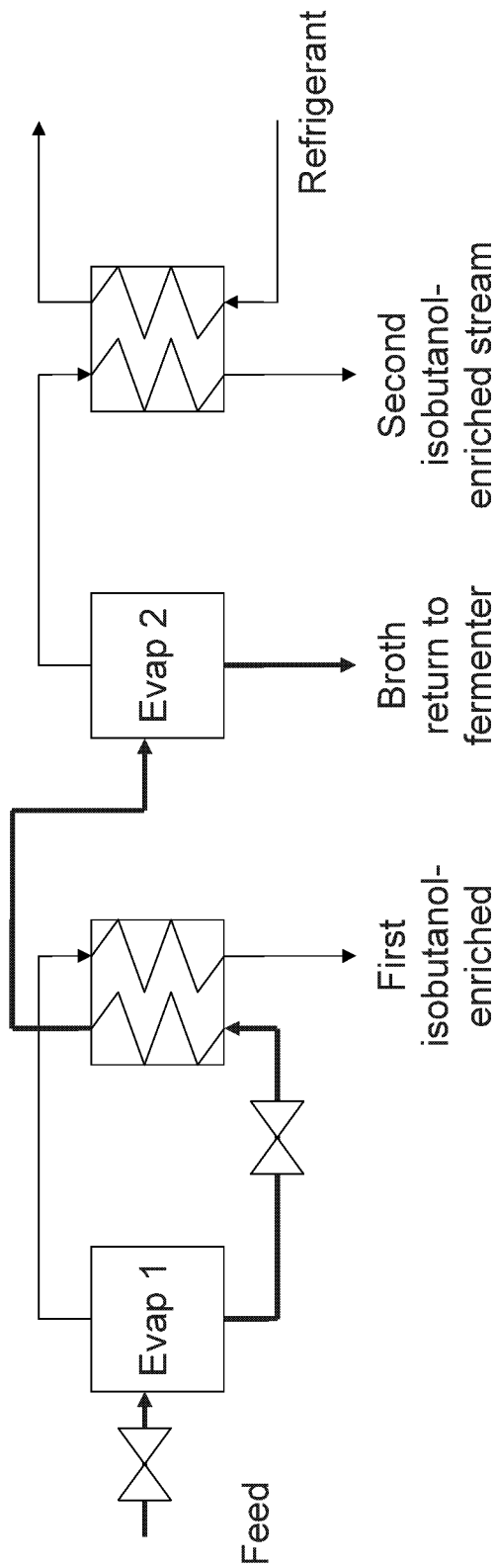
FIG. 10 is a flowsheet illustrating a two-effect refrigerative evaporation system, as described in Example 7.

This example examines a two-effect refrigerative evaporation system. A flowsheet illustrating the system is shown in FIG. 10. One significant advantage of this approach is its relative simplicity, since there is no need to remove the organisms from the fermentation broth provided the organisms can tolerate low temperatures, such as down to 5° to 10° C.

As illustrated in FIG. 10, fermentation broth is flashed down to a lower pressure, which evaporates a mixture considerably enriched in isobutanol. The remaining broth is then flashed to an even lower pressure and fed into a heat exchanger, where it is contacted with the vapor from the first flash. This condenses the first vapor, and creates a second vapor stream, also considerably enriched in isobutanol. The second vapor stream is condensed against a refrigerant. The low temperature of the refrigerant induces the lower pressure. The two isobutanol enriched streams can be pumped to a distillation section for further processing. Subsequent purification is made easier by the streams phase splitting into one portion containing around 80 wt % isobutanol and another portion containing about 10 wt % isobutanol.

Simulations were carried out to estimate the likely conditions for a range of fermentation broth strengths, and the amount of refrigeration energy needed. These simulations show that for a broth strength of 0.71 wt % isobutanol (approximately the minimum inlet concentration that is practically workable), the evaporation stages are at 0.0461 bar and 0.0274 bar, respectively, and the chilling cools the broth to 19° C.

The refrigeration needed is about 0.546 kWh/gallon of isobutanol product.

TABLE 1

Two-Effect Refrigerative Evaporation System

| Broth strength (wt %) | Stage 1 pressure (bar a) | Stage 2 pressure (bar a) | Stage 1 temperature (° C.) | Stage 2 temperature (° C.) | Refrigeration power (kWh/gallon) |
|---|---|---|---|---|---|
| 0.71% | 0.0461 | 0.0274 | 27.2 | 18.9 | 0.546 |
| 1.00% | 0.0386 | 0.0230 | 24.3 | 16.3 | 0.376 |
| 1.29% | 0.0322 | 0.0193 | 21.4 | 13.6 | 0.310 |
| 1.58% | 0.0268 | 0.0160 | 18.6 | 10.9 | 0.270 |
| 1.87% | 0.0221 | 0.0133 | 15.7 | 8.2 | 0.239 |

As used herein the terms "having," "comprising," and "including" are open and inclusive expressions. Alternatively, the term "consisting" is a closed and exclusive expression. Should any ambiguity exist in construing any term in the claims or the specification, the intent of the drafter is toward open and inclusive expressions.

Regarding an order, number, sequence, and/or limit of repetition for steps in a method or process, the drafter intends no implied order, number, sequence, and/or limit of repetition for the steps to the scope of the invention, unless explicitly provided.

Regarding ranges, ranges are to be construed as including all points between upper and lower values, such as to provide support for all possible ranges contained between the upper and the lower values including ranges with no upper bound and/or lower bound.

It will be apparent to those skilled in the art that various modifications and variations can be made in the disclosed structures and methods without departing from the scope or spirit of the invention. Particularly, descriptions of any one embodiment can be freely combined with descriptions or other embodiments to result in combinations and/or variations of two or more elements or limitations. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A method of producing a renewable material, the method comprising:
    consuming at least a portion of a fermentation feedstock with a fermentation organism to produce a renewable material in fermentation broth, the fermentation feedstock and fermentation broth comprising water;
    lowering a pressure of the fermentation feedstock and/or the fermentation broth to or below a saturation pressure of the fermentation broth and generating a vapor enriched in renewable material; and
    separating at least a portion of the water from the fermentation feedstock or fermentation broth using one or more phase separation.

2. The method of claim 1, wherein the step of separating comprises a solid-liquid separation.

3. The method of claim 1, wherein the step of separating comprises a liquid-liquid separation.

4. The method of claim 1, wherein the step of separating comprises a solid-liquid separation and a liquid-liquid separation.

5. The method of claim 4, further comprising removing enthalpy from the fermentation feedstock and/or fermentation broth.

6. The method of claim 5 wherein the step of removing enthalpy comprises an endothermic reaction.

7. The method of claim 1, further comprising lowering a temperature of the fermentation feedstock and/or the fermentation broth below an incipient crystallization temperature.

8. The method of claim 7, comprising using fluidized bed heat exchangers for crystallization.

9. The method of claim 1, further comprising solidifying the water.

10. The method of claim 1, further comprising raising a temperature of the fermentation feedstock and/or the fermentation broth above a boiling point of the renewable material and generating a vapor enriched in renewable material.

11. The method of claim 1, wherein the step of separating at least a portion of water from the fermentation feedstock or fermentation broth occurs with at least a portion of the step of consuming at least a portion of the fermentation feedstock.

12. A method of producing a biofuel component, the method comprising:
consuming at least a portion of a lignocellulosic fermentation feedstock with a fermentation organism to produce ethanol in fermentation broth, the fermentation feedstock and fermentation broth comprising water;
cooling at least a portion of the fermentation feedstock or fermentation broth to solidify at least a portion of the water; and
separating at least a portion of the solidified water from the fermentation feedstock or fermentation broth using a solid-liquid phase separation.

13. The method of claim 12, further comprising pre-processing of the fermentation feedstock and/or fermentation broth prior to phase separation.

14. The method of claim 12, further comprising separating broth particulates from the fermentation feedstock and/or fermentation broth before cooling at least a portion of the fermentation feedstock or fermentation broth and separating at least a portion of the solidified water from the fermentation feedstock or fermentation broth.

15. A method of producing a biofuel component, the method comprising:
consuming at least a portion of a sugar fermentation feedstock with a fermentation organism to produce butanol in fermentation broth, the fermentation feedstock and fermentation broth comprising water and other components;
cooling at least a portion of the fermentation feedstock or fermentation broth to solidify at least a portion of the water; and
separating at least a portion of the solidified water from the fermentation feedstock or fermentation broth using a solid-liquid phase separation.

* * * * *